(12) United States Patent
Walewski et al.

(10) Patent No.: US 11,154,591 B2
(45) Date of Patent: Oct. 26, 2021

(54) METHODS OF TREATING ALCOHOL ABUSE DISORDER

(71) Applicant: THE TRUSTEES OF COLUMBIA UNIVERSITY IN THE CITY OF NEW YORK, New York, NY (US)

(72) Inventors: José Leonardo Walewski, Fairfield, CT (US); Paul David Berk, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/341,803

(22) PCT Filed: Oct. 13, 2017

(86) PCT No.: PCT/US2017/056585
§ 371 (c)(1),
(2) Date: Apr. 12, 2019

(87) PCT Pub. No.: WO2018/071814
PCT Pub. Date: Apr. 19, 2018

(65) Prior Publication Data
US 2019/0314457 A1 Oct. 17, 2019

Related U.S. Application Data

(60) Provisional application No. 62/408,196, filed on Oct. 14, 2016.

(51) Int. Cl.
*A61K 38/22* (2006.01)
*A61P 25/32* (2006.01)

(52) U.S. Cl.
CPC .............. *A61K 38/22* (2013.01); *A61P 25/32* (2018.01)

(58) Field of Classification Search
CPC .................................. A61K 38/22; A61P 25/32
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,683,195 A | 7/1987 | Mullis et al. |
| 4,683,202 A | 7/1987 | Mullis |
| 4,710,384 A | 12/1987 | Rotman |
| 5,059,595 A | 10/1991 | Le Grazie |
| 5,073,543 A | 12/1991 | Marshall et al. |
| 5,120,548 A | 6/1992 | McClelland et al. |
| 5,236,838 A | 8/1993 | Rasmussen et al. |
| 5,252,479 A | 10/1993 | Srivastava |
| 5,328,470 A | 7/1994 | Nabel et al. |
| 5,354,556 A | 10/1994 | Sparks et al. |
| 5,391,377 A | 2/1995 | Barnwell |
| 5,580,757 A | 12/1996 | Desnick et al. |
| 5,591,767 A | 1/1997 | Mohr et al. |
| 5,639,476 A | 6/1997 | Oshiack et al. |
| 5,674,533 A | 10/1997 | Santus et al. |
| 5,733,566 A | 3/1998 | Lewis |
| 5,747,469 A | 5/1998 | Roth et al. |
| 5,879,680 A | 3/1999 | Ginns et al. |
| 6,017,524 A | 1/2000 | Roth et al. |
| 6,083,725 A | 7/2000 | Selden et al. |
| 6,143,290 A | 11/2000 | Zhang et al. |
| 6,188,045 B1 | 2/2001 | Hansen et al. |
| 6,210,666 B1 | 4/2001 | Miyamura |
| 6,255,497 B1 | 7/2001 | Vallee et al. |
| 6,395,884 B1 | 5/2002 | Selden et al. |
| 6,410,010 B1 | 6/2002 | Zhang et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,511,847 B1 | 1/2003 | Zhang et al. |
| 8,003,704 B2 | 8/2011 | Badawy |
| 9,057,726 B2 * | 6/2015 | Leroy .................. G01N 33/566 |
| 2002/0000069 A1 | 1/2002 | McNamara |
| 2002/0077313 A1 | 6/2002 | Clayman |
| 2005/0221359 A1 | 10/2005 | Hsueh et al. |
| 2005/0238639 A1 | 10/2005 | Conrad et al. |
| 2008/0261913 A1 | 10/2008 | Sommadossi et al. |
| 2010/0113473 A1 | 5/2010 | Player et al. |
| 2013/0196348 A1 | 8/2013 | Leroy |
| 2013/0274181 A1 | 10/2013 | Walewski et al. |

FOREIGN PATENT DOCUMENTS

| | | |
|---|---|---|
| EP | 2627349 B1 | 8/2013 |
| WO | WO-2006017171 A2 | 2/2006 |
| WO | WO-2012051567 A2 | 4/2012 |
| WO | WO-2018071814 A1 | 4/2018 |

OTHER PUBLICATIONS

Altaras, N.E. et al., "Production and Formulation of Adenovirus Vectors", Adv Biochem Engin Biotechnol, 99:193-260, Nov. 1, 2005 (68 pages).
Anderson, W.F., "Human gene therapy", Nature, Supplement to 392(6679):25-30, Apr. 30, 1998 (7 pages).
Anderson, W. F., "Hume Gene Therapy", Science, 256:808-813, May 8, 1992 (7 pages).
Barringer, K.J et al., "Blunt-end and single-strand ligations by *Escherichia coli* ligase: influence on an in vitro amplification scheme," Gene, 89:117-122, 1990 (6 pages).
Brower, V., "Naked DNA vaccines come of age", Nature Biotechnology, 16:1304-1305, Dec. 1998 (2 pages).
Buchwald, H., et al., "Long-term, continuous intravenous heparin administration by an implantable infusion pump in ambulatory patients with recurrent venous thrombosis", Surgery, 88(4):507-516 Oct. 1980 (12 pages).
Burg, J. L. et al., "Single molecule detection of RNA reporter probes by amplification with Qβ replicase", Molecular and Cellular Probes, 10:257-271, 1996 (15 pages).

(Continued)

*Primary Examiner* — Olga N Chernyshev
(74) *Attorney, Agent, or Firm* — Wilmer Cutler Pickering Hale and Dorr LLP

(57) ABSTRACT

The invention provides for methods of treating alcohol abuse disorder.

3 Claims, 1 Drawing Sheet
Specification includes a Sequence Listing.

(56) References Cited

OTHER PUBLICATIONS

Chen, S-H. et al., "Gene therapy for brain tumors: Regression of experimental gliomas by adenovirus-mediated gene transfer in vivo", Proc. Natl. Acad. Sci. USA, 91:3054-3057, Apr. 1994 (4 pages).
During, M.J. et al., "Controlled Release of Dopamine from a Polymeric Brain Implant: In Vivo Characterization", Annals of Neurology, 25(4):351-356, Apr. 1989 (6 pages).
Dzau, V.J. et al., "Gene therapy for cardiovascular disease", TIBTECH, 11:205-210, May 1993 (6 pages).
Eliyahu, H. et al., "Polymers for DNA Delivery", Molecules, 10:34-64, Jan. 31, 2005 (31 pages).
Fix, J.A., "Oral Controlled Release Technology for Peptides: Status and Future Prospects", Pharm Res, 13(12): 1760-1764, 1996 (5 pages).
Friedmann, T., "Progress Toward Human Gene Therapy", Science, 244:1275-1281, Jun. 16, 1989 (8 pages).
Goodson, J. M., "Chapter 6: Dental Applications", *Medical Applications of Controlled Release, vol. II: Applications and Evaluation*, Langer, et al. Eds., CRC Press, Inc., Boca Raton Florida, pp. 115-138, 1984 (26 pages).
Guatelli, J.C et al., "Isothermal, in vitro amplification of nucleic acids by a multienzyme reaction modeled after retroviral replication", Proc. Natl. Acad. Sci. USA, 87:1874-1878, Mar. 1990 (5 pages).
Herweijer, H et al., "Gene therapy progress and prospects: Hydrodynamic gene delivery", Gene Therapy, 14:99-107, published online Nov. 30, 2006 (9 pages).
Howard, M.A., III et al., "Intracerebral drug delivery in rats with lesion-induced memory deficits", J Neurosurg, 71:105-112, Jul. 1989 (8 pages).
International Preliminary Report on Patentability for International Patent Application No. PCT/US2017/056585, dated Apr. 16, 2019 (9 pages).
International Search Report and Written Opinion issued by the U.S. Patent and Trademark Office as International Searching Authority for International Patent Application No. PCT/US17/56585 dated Feb. 9, 2018 (12 pages).
Isaka, Y. et al., "Electroporation-mediated gene therapy", Expert Opin. Drug Deliv., 4(5):561-571, published online Sep. 20, 2007 (12 pages).
Jager, L. et al., "Emerging Adenoviral Vectors for Stable Correction of Genetic Disorders", Current Gene Therapy, 7(4):272-283, 2007 (12 pages).
Jensen, T.G., "Cutaneous gene therapy", Annals of Medicine., 39:108-115, 2007 (8 pages).
Jonas, D.E et al., "Pharmacotherapy for Adults with Alcohol Use Disorders in Outpatient Settings: A Systematic Review and Meta-analysis", JAMA, 311 (18), 1889-1900, May 14, 2014 (12 pages).
Kikuchi, Y et al., "Cutaneous gene delivery", Journal of Dermatological Science 50:87-98, 2008 (12 pages).
Kim, D-K et al., "Coevolution of the Spexin/Galanin/Kisspeptin Family: Spexin Activates Galanin Receptor Type II and III", Endocrinology, 155 (5): 1864-1873, May 2014 (10 pages).
Kimmel, A.R et al., "Preparation of cDNA and the Generation of cDNA Libraries: Overview", Methods in Enzymology, 152:307-316, 1987 (10 pages).
Kushner, M.G et al., "The Relationship Between Anxiety Disorders and Alcohol Use Disorders: A Review of Major Perspectives and Findings", Clinical Psychology Review, 20(2): 149-171,2000 (23 pages).
Kwoh, D.Y et al., "Transcription-based amplification system and detection of amplified human immunodeficiency virus type 1 with a bead-based sandwich hybridization format", Proc. Natl. Acad. Sci. USA, 86:1173-1177, Feb. 1989 (5 pages).
Landegren, U. et al., "A Ligase-Mediated Gene Detection Technique", Science, 241:1077-1080, Aug. 26, 1988 (4 pages).

Langer, R., "New Methods of Drug Delivery", Science, 249:1527-1533, Sep. 28, 1990 (8 pages).
Langer, R et al., "Chemical and Physical Structure of Polymers as Carriers for Controlled Release of Bioactive Agents: A Review", Journal of Macromolecular Science—Reviews in Macromolecular Chemistry and Physics, 23:1,61-126, 1983 (67 pages).
Levy, R.J et al., "Inhibition of Calcification of Bioprosthetic Heart Valves by Local Controlled-Release Disphosphonate", Science, 228:190-192, Apr. 12, 1985 (3 pages).
Mason, B.J et al., "Acamprosate: A prototypic neuromodulator in the treatment of alcohol dependence", Author manuscript, published in final edited form as: CNS Neurol Disord Drug Targets, 9(1): 23-32 , Mar. 2010 (21 pages).
Mason, B.J et al., "The neurobiology, clinical efficacy and safety of acamprosate in the treatment of alcohol dependence", Expert Opinion on Drug Safety, 9(1):177-188, published online Dec. 20, 2009 (13 pages).
Miller, A. D., "Human gene therapy comes of age", Nature, 357:455-460, Jun. 11, 1992 (6 pages).
Miller, P.M. et al., "Medical Treatment of Alcohol Dependence: A Systematic Review", Author Manuscript, published in final edited form as: Int J Psychiatry Med., 42(3):227-266, 2011 (30 pages).
Mirabeau, O. et al., "Identification of novel peptide hormones in the human proteome by hidden Markov model screening", Genome Research, 17:320-327, 2007 (8 pages).
Ogborne, A.C., "Identifying and treating patients with alcohol-related problems", CMAJ, 162(12): 1705-1708, Jun. 13, 2000 (4 pages).
Reyes-Alcaraz, A et al., "Development of Spexin-based Human Galanin Receptor Type II-Specific Agonists with Increased Stability in Serum and Anxiolytic Effect in Mice", Scientific Reports, 6:21453, Feb. 24, 2016 (10 pages).
Rösner, S. et al., "Acamprosate for alcohol dependence (Review)", Cochrane Database of Systematic Reviews, Issue 9, Article No. CD004332, 2010 (139 pages).
Samanen, J. et al., "Chemical Approaches to Improve the Oral Bioavailability of Peptidergic Molecules", J. Pharm Pharmacol., 48:119-135, 1996 (17 pages).
Saudek, C.D. et al., "A Preliminary Trial of the Programmable Implantable Medication System for Insulin Delivery", New England Journal of Medicine, 321 (9):574-579, Aug. 31, 1989 (6 pages).
Sefton, M.V., "Implantable Pumps", *CRC Critical Reviews in Biomedical Engineering*, Bourne, Ed., CRC Press, Boca Raton, Florida, 14(3):201-240, 1987 (42 pages).
Sinclair, J.D., "Evidence About the Use of Naltrexone and for Different Ways of Using It in the Treatment of Alcoholism", Alcohol and Alcoholism, 36(1): 2-10,2001 (12 pages).
Smith, J.H. et al., "Detection of *Mycobacterium tuberculosis* Directly from Sputum by Using a Prototype Automated Q-Beta Replicase Assay", J. Clin. Microbiol., 35(6):1477-1483, Jun. 1997 (7 pages).
Soyka, M. et al., "Opioid Antagonists for Pharmacological Treatment of Alcohol Dependence—A Critical Review", Current Drug Abuse Reviews, 1(3):280-291, 2008 (12 pages).
Sooknanan, R et al., "NASBA: A detection and amplification system uniquely suited for RNA", Bio/Technology, 13:563-564, Jun. 13, 1995 (2 pages).
Substance Abuse and Mental Health Services Administration, "Results from the 2010 National Survey on Drug Use and Health: Summary of National Findings." NSDUH Series H-41, HHS Publication No. (SMA) 11-4658, Rockville, MD: Substance Abuse and Mental Health Services Administration, Sep. 2011 (156 pages).
Suchankova, P. et al., "The glucagon-like peptide-1 receptor as a potential treatment target in alcohol use disorder: evidence from human genetic association studies and a mouse model of alcohol dependence", Translational Psychiatry, 5, e583, published online Jun. 16, 2015 (11 pages).
Toll, L. et al., "Peptides derived from the prohormone proNPQ/spexin are potent central modulators of cardiovascular and renal function and nociception," FASEB J., 26(2):947-954, Feb. 2012 (17 pages).
U.S. Department of Health and Human Services, "Alcohol Alert: Alcohol and Other Drugs", National Institute on Alcohol Abuse and Alcoholism, No. 76, Jul. 2008 (6 pages).

(56) References Cited

OTHER PUBLICATIONS

Verma, I.M., "Gene Therapy", Scientific American, pp. 68-72, 81-82, and 84, Nov. 1990 (10 pages).
Waehler, R et al., "Engineering targeted viral vectors for gene therapy", Nature Reviews/Genetics, 8:573-587, Aug. 2007 (15 pages).
Walewski, J.L et al., "Spexin Is a Novel Human Peptide that Reduces Adipocyte Uptake of Long Chain Fatty Acids and Causes Weight Loss in Rodents with Diet-Induced Obesity", Obesity, 22(7): 1643-1652, Jul. 2014 (10 pages).
Wu, D.Y et al., "The Ligation Amplification Reaction (LAR)-Amplification of Specific DNA Sequences Using Sequential Rounds of Template-Dependent Ligation", Genomics, 4: 560-569, 1989 (10 pages).
Bailey, K.R. et al., "Galanin Receptor Subtype 2 (GalR2) Null Mutant Mice Display an Anxiogenic-like Phenotype Specific to the Elevated Plus-maze", Author Manuscript, Published in final edited form as: Pharmacol Biochem Behav, 86(1):8-20, Jan. 2007 (23 pages).
Gu, L., et al., "Spexin peptide is expressed in human endocrine and epithelial tissues and reduced after glucose load in type 2 diabetes," Peptides, 71:232-239, 2015 (8 pages).
Porzionato, A. et al., "Spexin Expression in Normal Rat Tissues", Journal of Histochemistry & Cytochemistry, 58(9):825-837, 2010 (13 pages).
Robertson, C.R et al., "Engineering Galanin Analogues that Discriminate Between GalR1 and GalR2 Receptor Subtypes and Exhibit Anticonvulsant Activity Following Systemic Delivery", Author Manuscript, Published in final edited form as: J Med Chem, 53(4): 1871 -1875, Feb. 25, 2010 (15 pages).
Wan, B et al., "C12ORF39, a novel secreted protein with a typical amidation processing signal", Biosci. Rep., 30(1):1-10, 2010 (10 pages).
Webling, K. et al., "Ala$^5$-galanin (2-11) is a GAL$_2$R specific galanin analogue", Neuropeptides, 60: 75-82, Aug. 25, 2016 (8 pages).
Bognetti, E. et al., "Prevalence and correlates of obesity in insulin dependent diabetic patients", Archives of Disease in Childhood, 73:239-242, 1995 (5 pages).
European Supplemental Search Report issued by the European Patent Office for European Application No. 11833512.4 dated Mar. 27, 2014 (11 pages).

Jimenez-Cruz, A. et al., "Low glycemic index lunch on satiety in overweight and obese people with type 2 diabetes", Nutr. Hosp., 20(5):348-350, Sep.-Oct. 2005 (4 pages).
Orpana, H.M. et al., "BMI and Mortality: Results From a National Longitudinal Study of Canadian Adults", Obesity Journal, 18(1):214-218, Jan. 2010 (5 pages).
Walewski, J.L., et al., "Adipocyte Accumulation of Long-Chain Fatty Acids in Obesity is Multifactorial, Resulting from Increased Fatty Acid Uptake and Decreased Activity of Genes Involved in Fat Utilization", Author Manuscript, Published in final edited form as Obes Surg, 20(1): 93-107, Jan. 2010 (26 pages).
International Search Report and Written Opinion issued from the United States Patent Office as Searching Authority for Application No. PCT/US11/56417 dated Oct. 10, 2012 (17 pages).
Anderson, K., "Overcoming Addiction: Healing through harm reduction: Drink Your Way Sober with Naltrexone: Why have so few US doctors and therapists heard of The Sinclair Method?" [retrieved May 3, 2019], retrieved from the Internet <URL:https://archive.is/1OHab>, Psychology Today, Jul. 27, 2013 (3 pages).
GenBank Accession Nos. NM_030572, "*Homo sapiens* spexin hormone (SPX), transcript variant 1, mRNA", NCBI Reference Sequence: NM_030572.4, PRI Jan. 27, 2019, [retrieved on Apr. 9, 2019], retrieved from the internet:<URL:https://www.ncbi.nlm.nih.gov/nuccore/NM_030572.4?report=gbwithparts&log$=seq view> (4 pages).
National Institute on Alcohol Abuse and Alcoholism, "FAQs for the General Public", [retrieved on Dec. 9, 2011 ] retrieved from the Internet <URL:http://www.niaaa.nih.gov/FAQs/General-English/Pages/default.aspx#whatis>, Updated Feb. 2007 (4 pages).
RGD, "Gene: C12orf39 (chromosome 12 open reading frame 39) *Homo sapiens* ", Rat Genome Database [retrieved May 16, 2012], retrieved from the Internet <URL:http://rgd.mcw.edu/rgdweb/report/gene/main.html?id=1606773>, last modified Apr. 24, 2012 (2 pages).
Sandhyarani, N., "Serum Vs. Plasma", [retrieved on Jun. 25, 2014], retrieved from the internet <URL:http://www.buzzle.com/articles/serum-vs-plasma.html>, last updated Mar. 26, 2013 (3 pages).
Toll, L.R., et al., "NPQ/Spexin in Endogenous Ligand for the Galanin Receptor 3", NIH Project #: 1R01DA040882-01A1, Awardee Organization: Torrey Pines Institute for Molecular Studies [retrieved Oct. 15, 2020], retrieved from the Internet <URL:http://grantome.com/grant/NIH/R01-DA040882-01A1>, Fiscal Year 2016 (4 pages).
UniProtKB—Q9BT56 (SPXN_Human), Accession No. Q9BT56 [retrieved Apr. 9, 2019], retrieved from the Internet <URL:https://www.uniprot.org/uniprot/Q9BT56>, Integrated into UniProtKB/SwissProt: Sep. 27, 2005, Last modified: Feb. 13, 2019 (8 pages).

\* cited by examiner

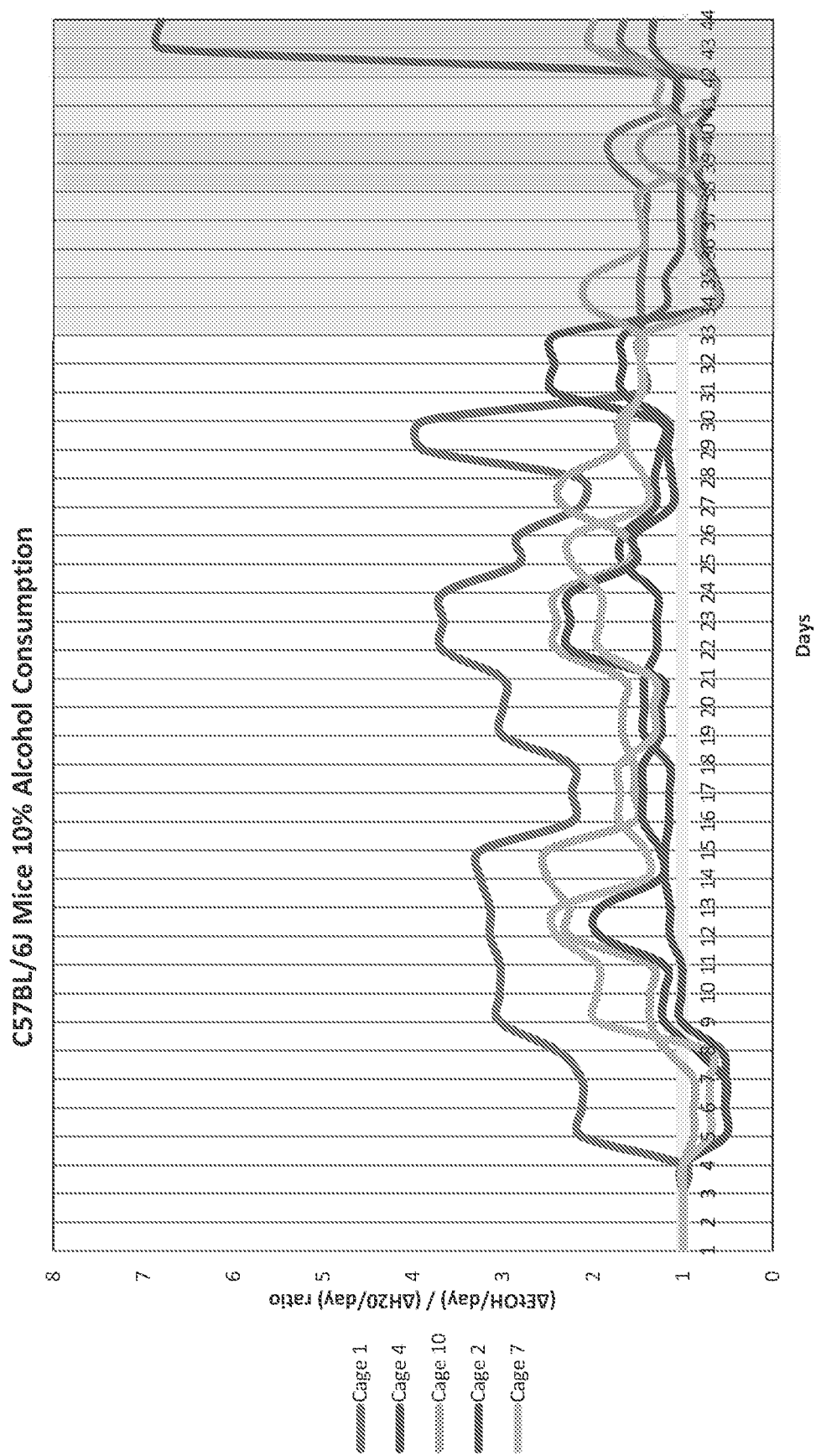

SEQUENCE LISTING

<160> NUMBER OF SEQ ID NOS: 11

<210> SEQ ID NO 1
<211> LENGTH: 116
<212> TYPE: PRT
<213> ORGANISM: Homo sapiens

<400> SEQUENCE: 1

```
Met Lys Gly Leu Arg Ser Leu Ala Ala Thr Thr Leu Ala Leu Phe Leu
1               5                   10                  15

Val Phe Val Phe Leu Gly Asn Ser Ser Cys Ala Pro Gln Arg Leu Leu
            20                  25                  30

Glu Arg Arg Asn Trp Thr Pro Gln Ala Met Leu Tyr Leu Lys Gly Ala
        35                  40                  45

Gln Gly Arg Arg Phe Ile Ser Asp Gln Ser Arg Arg Lys Asp Leu Ser
    50                  55                  60

Asp Arg Pro Leu Pro Glu Arg Arg Ser Pro Asn Pro Gln Leu Leu Thr
65                  70                  75                  80

Ile Pro Glu Ala Ala Thr Ile Leu Leu Ala Ser Leu Gln Lys Ser Pro
                85                  90                  95

Glu Asp Glu Glu Lys Asn Phe Asp Gln Thr Arg Phe Leu Glu Asp Ser
                100                 105                 110

Leu Leu Asn Trp
        115
```

<210> SEQ ID NO 2
<211> LENGTH: 638
<212> TYPE: DNA
<213> ORGANISM: Homo sapiens

<400> SEQUENCE: 2

```
ctgacaagat gtccctgtgg actcccaaac tctactccag atggggaggt gcccttaaca      60
ccaagatttt aaaagctcca atttcagagc aagagtcgaa aactcacaga taaagttata     120
gttatttcag ggttctgaaa agacgcagaa catgaaggga ctcagaagtc tggcagcaac     180
aaccttggct ctttctctgg tgtttgtttt cctgggaaac tccagctgcg ctccgcagag     240
actgttggag agaaggaact ggactcctca agctatgctc tacctgaaag gggcacaggg     300
tcgccgcttc atctccgacc agagccggag aaaggacctc tccgaccggc cactgccgga     360
```

-continued

```
aagacgaagc ccaaatcccc aactactaac tattccggag gcagcaacca tcttactggc    420
gtcccttcag aaatcaccag aagatgaaga aaaaaacttt gatcaaacca gattcctgga    480
agacagtctg cttaactggt gaaaatatac tggattatgt ttaattatgg ttctattctc    540
tttgaaaaca tgaaccatgt gaataaaacc tttggacccct ttttaaaaaa aaaaaaaaa    600 aaaaaaaaaa aaaaaaaaaa aaaaaaaaaa aaaaaaaa                             638
```

<210> SEQ ID NO 3
<211> LENGTH: 14
<212> TYPE: PRT
<213> ORGANISM: Homo sapiens

<400> SEQUENCE: 3

Asn Trp Thr Pro Gln Ala Met Leu Tyr Leu Lys Gly Ala Gln
1               5                   10

<210> SEQ ID NO 4
<211> LENGTH: 14
<212> TYPE: PRT
<213> ORGANISM: Homo sapiens

<400> SEQUENCE: 4

Asn Trp Thr Pro Gln Ala Met Leu Tyr Leu Lys Gly Ala Gln
1               5                   10

<210> SEQ ID NO 5
<211> LENGTH: 89
<212> TYPE: PRT
<213> ORGANISM: Homo sapiens

<400> SEQUENCE: 5

Pro Gln Arg Leu Leu Glu Arg Arg Asn Trp Thr Pro Gln Ala Met Leu
1               5                   10                  15

Tyr Leu Lys Gly Ala Gln Gly Arg Arg Phe Ile Ser Asp Gln Ser Arg
                20                  25                  30

Arg Lys Asp Leu Ser Asp Arg Pro Leu Pro Glu Arg Arg Ser Pro Asn
            35                  40                  45

Pro Gln Leu Leu Thr Ile Pro Glu Ala Ala Thr Ile Leu Leu Ala Ser
        50                  55                  60

Leu Gln Lys Ser Pro Glu Asp Glu Glu Lys Asn Phe Asp Gln Thr Arg
65                  70                  75                  80

Phe Leu Glu Asp Ser Leu Leu Asn Trp
                85

<210> SEQ ID NO 6
<211> LENGTH: 16
<212> TYPE: PRT
<213> ORGANISM: Homo sapiens

<400> SEQUENCE: 6

Asn Trp Thr Pro Gln Ala Met Leu Tyr Leu Lys Gly Ala Gln Gly Arg
1               5                   10                  15

<210> SEQ ID NO 7
<211> LENGTH: 17
<212> TYPE: PRT
<213> ORGANISM: Homo sapiens

```
<400> SEQUENCE: 7

Asn Trp Thr Pro Gln Ala Met Leu Tyr Leu Lys Gly Ala Gln Gly Arg
1               5                   10                  15

Arg

<210> SEQ ID NO 8
<211> LENGTH: 20
<212> TYPE: PRT
<213> ORGANISM: Homo sapiens

<400> SEQUENCE: 8

Arg Arg Phe Ile Ser Asp Gln Ser Arg Arg Lys Asp Leu Ser Asp Arg
1               5                   10                  15

Pro Leu Pro Glu
            20

<210> SEQ ID NO 9
<211> LENGTH: 21
<212> TYPE: PRT
<213> ORGANISM: Homo sapiens

<400> SEQUENCE: 9

Arg Arg Phe Ile Ser Asp Gln Ser Arg Arg Lys Asp Leu Ser Asp Arg
1               5                   10                  15

Pro Leu Pro Glu Arg
            20

<210> SEQ ID NO 10
<211> LENGTH: 22
<212> TYPE: PRT
<213> ORGANISM: Homo sapiens

<400> SEQUENCE: 10

Arg Arg Phe Ile Ser Asp Gln Ser Arg Arg Lys Asp Leu Ser Asp Arg
1               5                   10                  15

Pro Leu Pro Glu Arg Arg
            20

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5
```

METHODS OF TREATING ALCOHOL ABUSE DISORDER

This application is a National Stage Entry of PCT International Application Number PCT/US2017/056585, filed Oct. 13, 2017, which claims priority to U.S. Provisional Application No. 62/408,196, filed on Oct. 14, 2016, which is incorporated herein by reference in its entirety.

GOVERNMENT SUPPORT

This invention was made with government support under Grant No. U01-DK066667 awarded by the National Institutes of Health, and Grant No. DK026687 awarded by the New York Obesity and Nutrition Research Center (NYONRC) and National Institutes of Health/National Institute of Diabetes and Digestive and Kidney Diseases (NIDDK). The Government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Oct. 13, 2017, is named 19240_1120_SL.txt and is 4,809 bytes in size.

BACKGROUND OF THE INVENTION

For most adults, moderate alcohol use, i.e., no more than two drinks a day for men and one for women and older people is relatively harmless. Moderate use, however, lies at one end of a range that moves through alcohol abuse to alcohol dependence. Alcohol abuse is a drinking pattern that results in significant and recurrent adverse consequences. People with alcoholism, also known as known as "alcohol dependence", have lost reliable control of their alcohol use. Alcohol-dependent people are often unable to stop drinking once they start. Alcohol dependence is characterized by tolerance (i.e., the need to drink more to achieve the same "high") and withdrawal symptoms if drinking is suddenly stopped. Withdrawal symptoms may include nausea, sweating, restlessness, irritability, tremors, hallucinations and convulsions.

SUMMARY OF THE INVENTION

The present invention provides methods that are useful for the treatment of alcohol abuse disorder.

As would be apparent to one of ordinary skill in the art, any method or composition described herein can be implemented with respect to any other method or composition described herein.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

In certain aspects, the invention provides a method of treating alcohol abuse disorder in a subject in need thereof, comprising administering to the subject an effective amount of Spexin. In one embodiment, the subject is a human or non-human animal. In another embodiment, the non-human animal is a mouse, rat, dog, or cat.

In certain aspects the invention provides, a method for treating alcohol abuse disorder in a subject, the method comprising administering to a subject an effective amount of Spexin.

In certain aspects the invention provides a method for treating alcohol abuse disorder in a subject, the method comprising administering to a subject in need thereof a polypeptide comprising SEQ ID NO: 1, or a pharmaceutically acceptable salt thereof.

In certain aspects the invention provides a method for treating alcohol abuse disorder in a subject, the method comprising administering to a subject in need thereof a polypeptide comprising SEQ ID NO: 3 or 4, or a pharmaceutically acceptable salt thereof.

In certain aspects the invention provides a method for reducing alcohol consumption in a subject afflicted with alcohol abuse disorder, the method comprising administering to the subject an effective amount of Spexin. In some embodiments, the consumption of alcohol by the subject is reduced compared to the consumption of alcohol by the subject before administration of the polypeptide.

In certain aspects the invention provides, a method for reducing alcohol consumption in a subject afflicted with alcohol abuse disorder, the method comprising administering to the subject a polypeptide comprising SEQ ID NO: 1, or a pharmaceutically acceptable salt thereof. In some embodiments, the consumption of alcohol by the subject is reduced compared to the consumption of alcohol by the subject before administration of the polypeptide.

In certain aspects the invention provides, a method for reducing alcohol consumption in a subject afflicted with alcohol abuse disorder, the method comprising administering to the subject a polypeptide comprising SEQ ID NO: 3 or 4, or a pharmaceutically acceptable salt thereof. In some embodiments, the consumption of alcohol by the subject is reduced compared to the consumption of alcohol by the subject before administration of the polypeptide.

In certain aspects the invention provides, a method for promoting the cessation of alcohol consumption in a subject afflicted with alcohol abuse disorder, the method comprising administering to the subject an effective amount of Spexin. In some embodiments, the subject ceases consumption of alcohol.

In certain aspects the invention provides, a method for promoting the cessation of alcohol consumption in a subject afflicted with alcohol abuse disorder, the method comprising administering to the subject a polypeptide comprising SEQ ID NO: 1, or a pharmaceutically acceptable salt thereof. In some embodiments, the subject ceases consumption of alcohol.

In certain aspects the invention provides, a method for promoting the cessation of alcohol consumption in a subject afflicted with alcohol abuse disorder, the method comprising administering to the subject a polypeptide comprising SEQ ID NO: 3 or 4, or a pharmaceutically acceptable salt thereof. In some embodiments, the subject ceases consumption of alcohol.

In some embodiments, the subject is a human or non-human animal. In some embodiments, the subject is male and consumes more than 3 ounces of alcohol per day. In some embodiments, the subject is female and consumes more than 1.5 ounces of alcohol per day. In some embodiments, the subject is over 60 years of age and consumes more than 1.5 ounces of alcohol per day.

In some embodiments, the amount administered results in at least about 1 ng/ml in the serum. In some embodiments, the amount administered results in at least about 3 ng/ml in the serum. In some embodiments, the amount administered results in at least about 10 ng/ml in the serum. In some embodiments, the amount administered results in at least about 30 ng/ml in the serum. In some embodiments, the amount administered results in at least about 100 ng/ml in the serum. In some embodiments, the amount administered results in at least about 250 ng/ml in the serum. In some embodiments, the amount administered results in at least about 500 ng/ml in the serum.

In some embodiments, the polypeptide is administered at least once daily or at least twice daily. In some embodiments, the polypeptide is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks. In some embodiments, the polypeptide is administered for at least 1 year, for at least 1.5 years, for at least 2 years, for at least 2.5 years, or for at least 5 years.

BRIEF DESCRIPTION OF THE FIGURES

FIG. 1 shows a plot of the ratio of 10% EtOH/water consumption over time in C57BL/6J Mice. Cage(s) 1, 4, and 10 are Spexin-treated caged mice. Cage(s) 2 & 7 are PBS-treated caged mice. The first treatment cycle began on Day 33 through Day 37. The second treatment was on Day 40. No treatment was administered on Day(s) 38, 39, and after Day 41.

DETAILED DESCRIPTION OF THE INVENTION

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

The terms "animal," "subject" and "patient" as used herein includes all members of the animal kingdom including, but not limited to, mammals, animals (e.g., cats, dogs, horses, swine, etc.) and humans. A subject, according to the invention includes, but is not limited to a human.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, 21$^{st}$ Edition (University of the Sciences in Philadelphia, ed., Lippincott Williams & Wilkins 2005); and Handbook of Pharmaceutical Excipients, 7$^{th}$ Edition (Raymond Rowe et al., ed., Pharmaceutical Press 2012); each hereby incorporated by reference in its entirety.

In certain aspects, the invention provides a method of treating alcohol abuse disorder in a subject in need thereof, comprising administering to the subject an effective amount of Spexin. In some embodiments, the subject is a human.

The invention provides methods for administering Spexin or a polypeptide comprising SEQ ID NOs: 1, 3, or 4, or polypeptide derived from Spexin, or a pharmaceutically acceptable salt thereof, to a subject to treat alcohol abuse disorder. The invention also provides methods for administering Spexin or a polypeptide comprising SEQ ID NOs: 1, 3, or 4, or polypeptide derived from Spexin, or a pharmaceutically acceptable salt thereof, to subject afflicted with alcohol abuse disorder in order to reduce alcohol consumption or to promote cessation of alcohol consumption in the subject.

Alcohol Abuse Disorder

For most adults, moderate alcohol use, i.e., no more than two drinks a day for men and one for women and older people is relatively harmless. A "drink" means 1.5 ounces of spirits, 5 ounces of wine, or 12 ounces of beer, all of which contain 0.5 ounces of alcohol. Moderate use, however, lies at one end of a range that moves through alcohol abuse to alcohol dependence. Alcohol abuse is a drinking pattern that results in significant and recurrent adverse consequences. Alcohol abusers may fail to fulfill major school, work, or family obligations. They may have drinking-related legal problems, such as repeated arrests for driving while intoxicated. They may have relationship problems related to their drinking. People with alcoholism, also known as known as "alcohol dependence", have lost reliable control of their alcohol use. Alcohol-dependent people are often unable to stop drinking once they start. Alcohol dependence is characterized by tolerance (i.e., the need to drink more to achieve the same "high") and withdrawal symptoms if drinking is suddenly stopped. Withdrawal symptoms may include nausea, sweating, restlessness, irritability, tremors, hallucinations, and convulsions.

As used herein "alcohol abuse disorder" refers to a spectrum of disorders from alcohol abuse to alcohol dependence, including alcoholism. Alcohol abuse disorder can be characterized by a pattern of alcohol use that involves problems controlling your drinking, being preoccupied with alcohol, and/or continuing to use alcohol even when it causes problems. Substance use disorders occur when the recurrent use of alcohol and/or drugs causes clinically and functionally significant impairment, such as health problems, disability, and failure to meet major responsibilities at work, school, or home. In addition, tolerance to alcohol can be observed when a patient has to drink more to get the same pharmacologic effect "euphoria", or when the patient experiences withdrawal symptoms when they rapidly decrease or stop drinking. Normal alcohol consumption can vary among species and individuals based on a variety of factors. A diagnosis of substance use disorder, such as alcohol abuse disorder, is based on evidence of impaired control, social impairment, risky use, and pharmacological criteria.

Although severe alcohol problems get the most public attention, even mild to moderate problems cause substantial damage to individuals, their families and the community. According to the National Institute on Alcohol Abuse and Alcoholism (NIAAA), 1 in 12 American adults is an alcohol abuser or alcoholic (National Institute on Alcohol Abuse and Alcoholism. (2007). "FAQs for the general public."). Young adults aged 18 to 29 are the most likely to have alcohol problems. For example, a government survey revealed that almost 8 percent of young people aged 12 to 17 and almost 41 percent of young adults aged 18 to 25 indulge in binge drinking (drinking five or more drinks on the same occasion at least once during the past month) (Substance Abuse and Mental Health Services Administration. (2011). "Results from the 2010 National Survey on Drug Use and Health: Summary of national findings." NSDUH Series H-41, HHS Publication No. (SMA) 11-4658).

Problem drinking has multiple causes, with genetic, physiological, psychological, and social factors all playing a role. Not every individual is equally affected by each cause. For some alcohol abusers, psychological traits such as impulsiveness, low self-esteem and a need for approval prompt inappropriate drinking. Some individuals drink to cope with emotional problems. Social and environmental factors such as peer pressure and the easy availability of alcohol can play key roles. Poverty and physical or sexual abuse also increase the odds of developing alcohol dependence.

Genetic factors make some people especially vulnerable to alcohol dependence. A family history of alcohol problems doesn't mean that children will automatically grow up to have the same problems. Nor does the absence of family drinking problems necessarily protect children from developing these problems.

Once people begin drinking excessively, the problem can perpetuate itself. Heavy drinking can cause physiological changes that make continued drinking (i.e. alcohol consumption) the only way to avoid discomfort. Individuals with alcohol dependence may drink partly to reduce or avoid withdrawal symptoms.

While some research suggests that small amounts of alcohol may have beneficial cardiovascular effects, there is widespread agreement that heavier drinking can lead to health problems. Short-term effects include memory loss, hangovers, and blackouts. Long-term problems associated with heavy drinking include stomach ailments, heart problems, cancer, brain damage, serious memory loss and liver cirrhosis. Heavy drinkers also markedly increase their chances of dying from automobile accidents, homicide, and suicide.

Drinking problems also have a very negative impact on mental health. Alcohol abuse and alcoholism can worsen existing conditions such as depression or induce new problems such as serious memory loss, depression or anxiety.

Spexin

Spexin is a peptide with gastrointestinal activity. It was first identified using Markov modeling analysis based on features common to peptide hormones to find new ones in human proteome sequences (Mirabeau et al., (2007) Genome Res., 17: 320-327). It demonstrates contractile effects in a rat stomach explant assay, indicating a biological activity.

SEQ ID NO: 1 corresponds to the polypeptide sequence of human Spexin. SEQ ID NO: 2 corresponds to the nucleotide sequence of human Spexin. SEQ ID NOs: 3 and 4 corresponds to fragments of the Spexin polypeptide. Sequence information related to Spexin is accessible in public databases by GenBank Accession numbers NM_030572 (for mRNA) and NP_085049 (for protein).

SEQ ID NO: 1 is the human wild type amino acid sequence corresponding to Spexin (residues 1-116):

```
  1 MKGLRSLAAT TLALFLVFVF LGNSSCAPQR LLERRNWTPQ AMLYLKGAQG RRFISDQSRR

61 KDLSDRPLPE RRSPNPQLLT IPEAATILLA SLQKSPEDEE KNFDQTRFLE DSLLNW
```

SEQ ID NO: 2 is the human wild type nucleotide sequence corresponding to Spexin (nucleotides 1-638), wherein the underscored bolded "ATG" denotes the beginning of the open reading frame:

```
  1 ctgacaagat gtccctgtgg actcccaaac tctactccag atggggaggt gcccttaaca 61 ccaagatttt aaaagctcca atttcagagc aagagtcgaa aactcacaga taaagttata 121 gttatttcag ggttctgaaa agacgcagaa catgaaggga ctcagaagtc tggcagcaac
```

```
-continued
181 aaccttggct cttttcctgg tgtttgtttt cctgggaaac tccagctgcg ctccgcagag 241 actgttggag agaaggaact ggactcctca agctatgctc tacctgaaag gggcacaggg 301 tcgccgcttc atctccgacc agagccggag aaaggacctc tccgaccggc cactgccgga 361 aagacgaagc ccaaatcccc aactactaac tattccggag gcagcaacca tcttactggc 421 gtcccttcag aaatcaccag aagatgaaga aaaaaacttt gatcaaacca gattcctgga 481 agacagtctg cttaactggt gaaaatatac tggattatgt ttaattatgg ttctattctc 541 tttgaaaaca tgaaccatgt gaataaaacc tttggaccct ttttaaaaaa aaaaaaaaaa 601 aaaaaaaaaa aaaaaaaaaa aaaaaaaaaa aaaaaaaa
```

The full-length polypeptide sequence of human Spexin (SEQ ID NO: 1) is a precursor for a variety of peptide fragments. For example, full-length Spexin contains "RR" residues which can be sites of cleavage. In addition, full-length Spexin contains a signal sequence (amino acid residues 1-27 of SEQ ID NO: 1) which can be removed.

SEQ ID NO: 5 is the human wild type amino acid sequence corresponding to Spexin without the signal sequence:

```
 1 PQRLLERRNW TPQAMLYLKG AQGRRFISDQ SRRKDLSDRP LPERRSPNPQ

51 LLTIPEAATI LLASLQKSPE DEEKNFDQTR FLEDSLLNW
```

Peptide fragments of Spexin include, but are not limited to, amino acid residues 36-49, 36-51, 36-52, 53-70, 53-71, and 53-72 of SEQ ID NO: 1 (See e.g., Toll et al., FASEB J. (2012), Vol. 26(2): 947-954, the contents of which is hereby incorporated by reference in its entirety). Spexin without the signal sequence (SEQ ID NO: 5) can also be cleaved to generate the fragments corresponding to amino acid residues 36-49, 36-51, 36-52, 53-70, 53-71, and 53-72 of SEQ ID NO: 1. The exact cleavage products of Spexin can depend on the details of the expression system, for example, the cleavage products can vary depending on whether Spexin is expressed in a prokaryotic or eukaryotic expression system.

SEQ ID NO: 3 is the amino acid sequence corresponding to a fragment of Spexin (amino acid residues 36-49 of SEQ ID NO: 1):

```
NWTPQAMLYLKGAQ
```

In some embodiments, the peptide of SEQ ID NO: 3 is amidated on its carboxy-terminus (NWTPQAMLYLK-GAQ-amide (SEQ ID NO:4)).

SEQ ID NO: 6 is the amino acid sequence corresponding to a fragment of Spexin (amino acid residues 36-51 of SEQ ID NO: 1):

```
NWTPQAMLYLKGAQGR
```

SEQ ID NO: 7 is the amino acid sequence corresponding to a fragment of Spexin (amino acid residues 36-52 of SEQ ID NO: 1):

```
NWTPQAMLYLKGAQGRR
```

SEQ ID NO: 8 is the amino acid sequence corresponding to a fragment of Spexin (amino acid residues 53-70 of SEQ ID NO: 1):

```
RRFISDQSRRKDLSDRPLPE
```

SEQ ID NO: 9 is the amino acid sequence corresponding to a fragment of Spexin (amino acid residues 53-71 of SEQ ID NO: 1):

```
RRFISDQSRRKDLSDRPLPER
```

SEQ ID NO: 10 is the amino acid sequence corresponding to a fragment of Spexin (amino acid residues 53-72 of SEQ ID NO: 1):

```
RRFISDQSRRKDLSDRPLPERR
```

As used herein, "Spexin" refers to the full-length polypeptide sequence of human Spexin (SEQ ID NO: 1), as well as fragments of Spexin of any length, including, but not limited to, the peptides of SEQ ID NOs: 3, 4, 5, 6, 7, 8, 9, or 10, and variants thereof. For example, the Spexin fragment can encompass any portion of at least about 8 consecutive amino acids of SEQ ID NO: 1. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 80 consecutive amino acids, at least about 90 consecutive amino acids, at least about 100 consecutive amino acids, at least about 110 consecutive amino acids, or at least about 115 consecutive amino acids of SEQ ID NO: 1. Fragments include all possible amino acid lengths between about 8 and about 115 amino acids, for example, lengths between about 10 and about 115 amino acids, between about 15 and about 115 amino acids, between about 20 and about 115 amino acids, between about 30 and about 115 amino acids, between about 40 and about 115 amino acids, between about 50 and about 115 amino acids, between about 60 and about 115 amino acids, between about 70 and about 115 amino acids, between about 80 and about 115 amino acids, between about 90 and about 115 amino acids, between about 100 and about 115 amino acids, or between about 110 and about 115 amino acids. For example, the Spexin fragment can encompass any portion of at least 8, 9, 10, 11, 12, 13, 14, 15, 16, 17, 18, 19, 20, 21, 22, 23, 24, 25, 26, 27, 28, 29, or 30 consecutive amino acids of SEQ ID NO: 1. For example, SEQ ID NOs: 3 and 4 are Spexin fragments of 14 consecutive amino acids of SEQ ID NO: 1.

In some embodiments, the invention encompasses use of variants of Spexin (i.e., variants of the full-length polypeptide sequence of human Spexin (SEQ ID NO: 1), as well variants of fragments of Spexin of any length, including, but not limited to, the peptides of SEQ ID NOs: 3, 4, 5, 6, 7, 8, 9, or 10). Such a variant can comprise a naturally-occurring variant due to allelic variations between individuals (e.g., polymorphisms), or alternative splicing forms, as well as non-naturally occurring variants. Such variants can include those having at least from about 46% to about 50% identity to SEQ ID NO: 1, or having at least from about 50.1% to about 55% identity to SEQ ID NO: 1, or having at least from about 55.1% to about 60% identity to SEQ ID NO: 1, or having from at least about 60.1% to about 65% identity to SEQ ID NO: 1, or having from about 65.1% to about 70% identity to SEQ ID NO: 1, or having at least from about 70.1% to about 75% identity to SEQ ID NO: 1, or having at least from about 75.1% to about 80% identity to SEQ ID NO: 1, or having at least from about 80.1% to about 85% identity to SEQ ID NO: 1, or having at least from about 85.1% to about 90% identity to SEQ ID NO: 1, or having at least from about 90.1% to about 95% identity to SEQ ID NO: 1, or having at least from about 95.1% to about 97% identity to SEQ ID NO: 1, or having at least from about 97.1% to about 99.9% identity to SEQ ID NO: 1. In some embodiments, a spexin variant includes those having 80, 81, 82, 83, 84, 85, 86, 87, 88, 89, 90, 91, 92, 93, 94, 95, 96, 97, 98, or 99% identity to SEQ ID NO: 1.

Spexin variants can also include those having at least from about 46% to about 50% identity to SEQ ID NOs: 3 or 4, or having at least from about 50.1% to about 55% identity to SEQ ID NOs: 3 or 4, or having at least from about 55.1% to about 60% identity to SEQ ID NOs: 3 or 4, or having from at least about 60.1% to about 65% identity to SEQ ID NOs: 3 or 4, or having from about 65.1% to about 70% identity to SEQ ID NOs: 3 or 4, or having at least from about 70.1% to about 75% identity to SEQ ID NOs: 3 or 4, or having at least from about 75.1% to about 80% identity to SEQ ID NOs: 3 or 4, or having at least from about 80.1% to about 85% identity to SEQ ID NOs: 3 or 4, or having at least from about 85.1% to about 90% identity to SEQ ID NOs: 3 or 4, or having at least from about 90.1% to about 95% identity to SEQ ID NOs: 3 or 4, or having at least from about 95.1% to about 97% identity to SEQ ID NOs: 3 or 4, or having at least from about 97.1% to about 99.9% identity to SEQ ID NOs: 3 or 4. In some embodiments, a Spexin variant includes those having 80, 81, 82, 83, 84, 85, 86, 87, 88, 89, 90, 91, 92, 93, 94, 95, 96, 97, 98, or 99% identity to SEQ ID NOs: 3 or 4.

Spexin variants can also include those having at least from about 46% to about 50% identity to SEQ ID NOs: 5, 6, 7, 8, 9, or 10, or having at least from about 50.1% to about 55% identity to SEQ ID NOs: 5, 6, 7, 8, 9, or 10, or having at least from about 55.1% to about 60% identity to SEQ ID NOs: 5, 6, 7, 8, 9, or 10, or having from at least about 60.1% to about 65% identity to SEQ ID NOs: 5, 6, 7, 8, 9, or 10, or having from about 65.1% to about 70% identity to SEQ ID NOs: 5, 6, 7, 8, 9, or 10, or having at least from about 70.1% to about 75% identity to SEQ ID NOs: 5, 6, 7, 8, 9, or 10, or having at least from about 75.1% to about 80% identity to SEQ ID NOs: 5, 6, 7, 8, 9, or 10, or having at least from about 80.1% to about 85% identity to SEQ ID NOs: 5, 6, 7, 8, 9, or 10, or having at least from about 85.1% to about 90% identity to SEQ ID NOs: 5, 6, 7, 8, 9, or 10, or having at least from about 90.1% to about 95% identity to SEQ ID NOs: 5, 6, 7, 8, 9, or 10, or having at least from about 95.1% to about 97% identity to SEQ ID NOs: 5, 6, 7, 8, 9, or 10, or having at least from about 97.1% to about 99.9% identity to SEQ ID NOs: 5, 6, 7, 8, 9, or 10. In some embodiments, a Spexin variant includes those having 80, 81, 82, 83, 84, 85, 86, 87, 88, 89, 90, 91, 92, 93, 94, 95, 96, 97, 98, or 99% identity to SEQ ID NOs: 5, 6, 7, 8, 9, or 10.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture. In another embodiment, the Spexin polypeptide or fragment can be modified, such as by glycosylations and/or acetylations and/or chemical reaction or coupling, and can contain one or several non-natural or synthetic amino acids.

In one embodiment, the invention encompasses methods for using a protein or polypeptide encoded by a nucleic acid, such as the sequence shown in SEQ ID NO: 2. The nucleic acid can be any type of nucleic acid, including genomic DNA, complementary DNA (cDNA), recombinant DNA, synthetic or semi-synthetic DNA, as well as any form of corresponding RNA. A cDNA is a form of DNA artificially synthesized from a messenger RNA template and is used to produce gene clones. A synthetic DNA is free of modifications that can be found in cellular nucleic acids and include, but are not limited to, histones and methylation. For example, a nucleic acid encoding Spexin can comprise a recombinant nucleic acid encoding such a protein. The nucleic acid can be a non-naturally occurring nucleic acid created artificially (such as by assembling, cutting, ligating or amplifying sequences). It can be double-stranded or single-stranded.

The invention further provides for nucleic acids that are complementary to a Spexin nucleic acid. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

In some embodiments, the nucleic acid sequence encoding Spexin is about 70%, about 75%, about 80%, about 85%, about 90%, about 93%, about 95%, about 97%, about 98%, or about 99% identical to SEQ ID NO: 2.

DNA and Polypeptides, Methods, and Purification Thereof

The present invention utilizes conventional molecular biology, microbiology, and recombinant DNA techniques available to one of ordinary skill in the art. Such techniques are well known to the skilled worker and are explained fully in the literature. See, e.g. "*DNA Cloning: A Practical Approach,*" Volumes I and II (D. N. Glover, ed., 1985); "Oligonucleotide Synthesis" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986): B. Perbal, "*A Practical Guide to Molecular Cloning*" (1984), and Sambrook, et al., "*Molecular Cloning: a Laboratory Manual*" ($3^{rd}$ edition, 2001). One skilled in the art can obtain a protein encoded by a Spexin nucleic acid, or a variant thereof, in several ways, which include, but are not limited to, isolating the protein via biochemical means or expressing a nucleotide sequence encoding the protein of interest by genetic engineering methods. For example, Spexin, or a variant thereof, can be obtained by purifying it from human cells expressing a Spexin nucleic acid, or by direct chemical synthesis.

Host cells which contain a nucleic acid encoding a Spexin polypeptide, and which subsequently express a protein encoded by a Spexin nucleic acid, can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding a Spexin polypeptide can be detected by DNA-DNA or DNA-RNA hybridization or amplification using probes or fragments of nucleic acids encoding a Spexin polypeptide.

Amplification methods include, e.g., polymerase chain reaction, PCR (*PCR Protocols, a Guide to Methods and Applications*, ed. Innis, Academic Press, N.Y., 1990 and *PCR Strategies*, 1995, ed. Innis, Academic Press, Inc., N.Y., ligase chain reaction (LCR) (see, e.g., Wu, Genomics 4:560, 1989; Landegren, Science 241:1077, 1988; Barringer, Gene 89:117, 1990); transcription amplification (see, e.g., Kwoh, Proc. Natl. Acad. Sci. USA 86:1173, 1989); and, self-sustained sequence replication (see, e.g., Guatelli, Proc. Natl. Acad. Sci. USA 87:1874, 1990); Q Beta replicase amplification (see, e.g., Smith, J. Clin. Microbiol. 35:1477-1491, 1997), automated Q-beta replicase amplification assay (see, e.g., Burg, Mol. Cell. Probes 10:257-271, 1996) and other RNA polymerase mediated techniques (e.g., NASBA, Cangene, Mississauga, Ontario); see also Berger, Methods Enzymol. 152:307-316, 1987; Sambrook; Ausubel; U.S. Pat. Nos. 4,683,195 and 4,683,202; Sooknanan, Biotechnology 13:563-564, 1995. All the references and patents stated herein are each incorporated by reference in their entireties.

A guide to the hybridization of nucleic acids is found in e.g., Sambrook, ed., *Molecular Cloning: A Laboratory Manual* ($3^{rd}$ Ed.), Vols. 1-3, Cold Spring Harbor Laboratory, 2001; *Current Protocols In Molecular Biology*, Ausubel, ed. John Wiley & Sons, Inc., New York, 1997; *Laboratory Techniques In Biochemistry And Molecular Biology: Hybridization With Nucleic Acid Probes, Part I. Theory and Nucleic Acid Preparation*, Tijssen, ed. Elsevier, N.Y., 1993. All the references stated herein are each incorporated by reference in their entireties.

In one embodiment, a fragment of Spexin nucleic acid can encompass any portion of at least about 8 consecutive nucleotides of SEQ ID NO: 2. In another embodiment, the fragment can comprise at least about 10 consecutive nucleotides, at least about 15 consecutive nucleotides, at least about 20 consecutive nucleotides, or at least about 30 consecutive nucleotides of SEQ ID NO: 2. Fragments can include all possible nucleotide lengths between about 8 and about 100 nucleotides, for example, lengths between about 15 and about 100 nucleotides, or between about 20 and about 100 nucleotides. Nucleic acid amplification-based assays involve the use of oligonucleotides selected from sequences encoding a polypeptide encoded by a Spexin nucleic acid, or are complimentary to it, to detect transformants which contain a nucleic acid encoding a Spexin protein or polypeptide.

Methods for detecting and quantifying Spexin polypeptides and Spexin polynucleotides in biological samples are known the art. For example, protocols for detecting and measuring the expression of a polypeptide encoded by a Spexin nucleic acid, using either polyclonal or monoclonal antibodies specific for the polypeptide are well established. Non-limiting examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a polypeptide encoded by a Spexin can be used, or a competitive binding assay can be employed. In one embodiment, expression of, under-, or over-expression of a Spexin polypeptide or Spexin mRNA can be determined. In one embodiment, a biological sample comprises, a blood sample, serum, cells (including whole cells, cell fractions, cell extracts, and cultured cells or cell lines), tissues (including tissues obtained by biopsy), body fluids (e.g., urine, sputum, amniotic fluid, synovial fluid), or from media (from cultured cells or cell lines). The methods of detecting or quantifying Spexin polynucleotides include, but are not limited to, amplification-based assays with signal amplification, hybridization based assays and combination amplification-hybridization assays. For detecting and quantifying Spexin polypeptides, an exemplary method is an immunoassay that utilizes an antibody or other binding agents that specifically bind to a Spexin polypeptide or epitope, for example, ELISA or RIA assays.

Labeling and conjugation techniques are known by those skilled in the art and can be used in various nucleic acid and amino acid assays. Methods for producing labeled hybridization or PCR probes for detecting sequences related to nucleic acid sequences encoding a Spexin protein, include, but are not limited to, oligolabeling, nick translation, end-labeling, or PCR amplification using a labeled nucleotide. Alternatively, a nucleic acid sequence encoding a Spexin polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

Host cells transformed with a nucleic acid sequence encoding a Spexin polypeptide, can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence encoding a Spexin polypeptide can be designed to contain signal sequences which direct secretion of soluble polypeptide molecules encoded by a Spexin nucleic acid, or a variant thereof, through a prokaryotic or eukaryotic cell membrane.

Other constructions can also be used to join a gene sequence encoding a Spexin polypeptide to a nucleotide sequence encoding a polypeptide domain which would facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Cleavable linker sequences (i.e., those specific for Factor Xa or enterokinase (Invitrogen, San Diego, Calif.)) can be included between the purification domain and a polypeptide encoded by a Spexin nucleic acid to facilitate purification. One such expression vector provides for expression of a fusion protein containing a polypeptide encoded by a Spexin nucleic acid and 6 histidine residues (SEQ ID NO: 11) preceding a thioredoxin or an enterokinase cleavage site. The histidine residues facilitate purification by immobilized metal ion affinity chromatography, while the enterokinase cleavage site provides a means for purifying the polypeptide encoded by a Spexin nucleic acid.

A Spexin polypeptide can be purified from any human or non-human cell which expresses the polypeptide, including those which have been transfected with expression constructs that express a Spexin protein. A purified Spexin polypeptide can be separated from other compounds which normally associate with the Spexin polypeptide in the cell, such as certain proteins, carbohydrates, or lipids, using methods practiced in the art. Non-limiting methods include size exclusion chromatography, ammonium sulfate fractionation, ion exchange chromatography, affinity chromatography, and preparative gel electrophoresis.

Spexin nucleic acid sequences comprising a sequence that encodes a polypeptide can be synthesized, in whole or in part, using chemical methods known in the art. Alternatively, a Spexin polypeptide (e.g., SEQ ID NOs: 1, 3, 4, 5, 6, 7, 8, 9, or 10), can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of Spexin polypeptides can be separately synthesized and combined using chemical methods to produce a full-length molecule. In one embodiment, a fragment of Spexin can encompass any portion of at least about 8, 9, 10, 11, 12, 13, 14 consecutive amino acids of SEQ ID NOs: 1, 3, 4, 5, 6, 7, 8, 9, or 10. In one embodiment, the fragment can comprise at least about 15, or 16 consecutive amino acids of SEQ ID NOs: 1, 5, 6, 7, 8, 9, or 10. In one embodiment, the fragment can comprise at least about 17 consecutive amino acids of SEQ ID NOs: 1, 5, 7, 8, 9, or 10. In one embodiment, the fragment can comprise at least about 18, 19, or 20 consecutive amino acids of SEQ ID NOs: 1, 5, 8, 9, or 10. In one embodiment, the fragment can comprise at least about 21 consecutive amino acids of SEQ ID NOs: 1, 5, 9, or 10. In one embodiment, the fragment can comprise at least about 22 consecutive amino acids of SEQ ID NOs: 1, 5, or 10. In one embodiment, the fragment can comprise at least about 23, 24, 25, 26, 27, 28, 29, or 30 consecutive amino acids of SEQ ID NOs: 1 or 5. Fragments include all possible lengths between about 8 and about 115 amino acids, for example, lengths between about 15 and about 115 amino acids, or between about 20 and about 115 amino acids.

A synthetic peptide can be substantially purified via high performance liquid chromatography (HPLC). The composition of a synthetic Spexin polypeptide can be confirmed by amino acid analysis or sequencing. Additionally, any portion of an amino acid sequence comprising a protein encoded by a Spexin nucleic acid can be altered during direct synthesis and/or combined using chemical methods with sequences from other proteins to produce a variant polypeptide or a fusion protein.

Treatment of Alcohol Abuse Disorder

Treatments for alcohol abuse disorder range from non-pharmaceutical to pharmaceutical interventions. Non-pharmaceutical interventions include, but are not limited to, psychiatric or psychological treatments. In addition to non-pharmaceutical treatments, in the United States there are four currently FDA-approved medications for alcoholism: disulfiram, two forms of naltrexone, and acamprosate. Acamprosate may stabilize the brain chemistry that is altered due to alcohol dependence via antagonizing the actions of glutamate, a neurotransmitter which is hyperactive in the post-withdrawal phase. Disulfiram prevents the elimination of acetaldehyde, a chemical the body produces when breaking down ethanol. Acetaldehyde itself is the cause of many hangover symptoms from alcohol use. The overall effect is severe discomfort when alcohol is ingested: an extremely fast-acting and long-lasting uncomfortable hangover. This discourages an alcoholic from drinking in significant amounts while they take the medicine. Naltrexone is a competitive antagonist for opioid receptors, effectively blocking the effects of endorphins and opiates. Naltrexone is used to decrease cravings for alcohol and encourage abstinence.

In some embodiments, Spexin is administered to a subject with alcohol abuse disorder to treat alcohol abuse disorder. In another embodiment, a polypeptide comprising SEQ ID NO: 1, a fragment or variant thereof, or a pharmaceutically acceptable salt thereof is administered to a subject with alcohol abuse disorder to treat alcohol abuse disorder. In another embodiment, a polypeptide comprising SEQ ID NOs: 3 or 4, a fragment or variant thereof, or a pharmaceutically acceptable salt thereof is administered to a subject with alcohol abuse disorder to treat alcohol abuse disorder. In another embodiment, a polypeptide consisting essentially of SEQ ID NOs: 3 or 4, or a pharmaceutically acceptable salt thereof is administered to a subject with alcohol abuse disorder to treat alcohol abuse disorder. In another embodiment, a polypeptide consisting of SEQ ID NOs: 3 or 4, or a pharmaceutically acceptable salt thereof is administered to a subject with alcohol abuse disorder to treat alcohol abuse disorder. In another embodiment, a polypeptide comprising 85, 86, 87, 88, 89, 90, 91, 92, 93, 94, 95, 96, 97, 98 or 99% identity to SEQ ID NOs: 3 or 4, or a pharmaceutically acceptable salt thereof is administered to a subject with alcohol abuse disorder to treat alcohol abuse disorder. In another embodiment, a polypeptide consisting of 85, 86, 87, 88, 89, 90, 91, 92, 93, 94, 95, 96, 97, 98 or 99% identity to SEQ ID NOs: 3 or 4, or a pharmaceutically acceptable salt thereof is administered to a subject with alcohol abuse disorder to treat alcohol abuse disorder.

In another embodiment, a polypeptide comprising SEQ ID NOs: 5, 6, 7, 8, 9, or 10, a fragment or variant thereof, or a pharmaceutically acceptable salt thereof is administered to a subject with alcohol abuse disorder to treat alcohol abuse disorder. In another embodiment, a polypeptide consisting essentially of SEQ ID NOs: 5, 6, 7, 8, 9, or 10, or a pharmaceutically acceptable salt thereof is administered to a subject with alcohol abuse disorder to treat alcohol abuse disorder. In another embodiment, a polypeptide consisting of SEQ ID NOs: 5, 6, 7, 8, 9, or 10, or a pharmaceutically acceptable salt thereof is administered to a subject with alcohol abuse disorder to treat alcohol abuse disorder. In another embodiment, a polypeptide comprising 85, 86, 87, 88, 89, 90, 91, 92, 93, 94, 95, 96, 97, 98 or 99% identity to SEQ ID NOs: 5, 6, 7, 8, 9, or 10, or a pharmaceutically acceptable salt thereof is administered to a subject with alcohol abuse disorder to treat alcohol abuse disorder. In another embodiment, a polypeptide consisting of 85, 86, 87, 88, 89, 90, 91, 92, 93, 94, 95, 96, 97, 98 or 99% identity to SEQ ID NOs: 5, 6, 7, 8, 9, or 10, or a pharmaceutically acceptable salt thereof is administered to a subject with alcohol abuse disorder to treat alcohol abuse disorder.

In some embodiments, Spexin is administered to a subject afflicted with alcohol abuse disorder to reduce alcohol consumption in the subject. In another embodiment, a polypeptide comprising SEQ ID NO: 1, a fragment or variant thereof, or a pharmaceutically acceptable salt thereof is administered to a subject afflicted with alcohol abuse disorder to reduce alcohol consumption in the subject. In another embodiment, a polypeptide comprising SEQ ID NOs: 3 or 4, a fragment or variant thereof, or a pharmaceutically acceptable salt thereof is administered to a subject afflicted with alcohol abuse disorder to reduce alcohol consumption in the subject. In another embodiment, a polypeptide consisting essentially of SEQ ID NOs: 3 or 4, or a pharmaceutically acceptable salt thereof is administered to a subject afflicted with alcohol abuse disorder to reduce alcohol consumption in the subject. In another embodiment, a polypeptide consisting of SEQ ID NOs: 3 or 4, or a pharmaceutically acceptable salt thereof is administered to a subject afflicted with alcohol abuse disorder to reduce alcohol consumption in the subject. In another embodiment, a polypeptide comprising 85, 86, 87, 88, 89, 90, 91, 92, 93, 94, 95, 96, 97, 98 or 99% identity to SEQ ID NOs: 3 or 4, or a pharmaceutically acceptable salt thereof is administered to a subject with alcohol abuse disorder to reduce alcohol consumption in the subject. In another embodiment, a polypeptide consisting of 85, 86, 87, 88, 89, 90, 91, 92, 93, 94, 95, 96, 97, 98 or 99% identity to SEQ ID NOs: 3 or 4, or a pharmaceutically acceptable salt thereof is administered to a subject with alcohol abuse disorder to reduce alcohol consumption in the subject. In some embodiments, the consumption of alcohol is reduced compared to the consumption of alcohol before administration of the polypeptides of the invention to the subject.

In another embodiment, a polypeptide comprising SEQ ID NOs: 5, 6, 7, 8, 9, or 10, a fragment or variant thereof, or a pharmaceutically acceptable salt thereof is administered to a subject afflicted with alcohol abuse disorder to reduce alcohol consumption in the subject.

In another embodiment, Spexin is administered to a subject afflicted with alcohol abuse disorder to promote cessation of alcohol consumption in the subject. In another embodiment, a polypeptide comprising SEQ ID NO: 1, a fragment or variant thereof, or a pharmaceutically acceptable salt thereof is administered to a subject afflicted with alcohol abuse disorder to promote cessation of alcohol consumption in the subject. In another embodiment, a polypeptide comprising SEQ ID NOs: 3 or 4, a fragment or variant thereof or a pharmaceutically acceptable salt thereof is administered to a subject afflicted with alcohol abuse disorder to promote cessation of alcohol consumption in the subject. In another embodiment, a polypeptide consisting essentially of SEQ ID NOs: 3 or 4, or a pharmaceutically acceptable salt thereof is administered to a subject afflicted with alcohol abuse disorder to promote cessation of alcohol consumption in the subject. In another embodiment, a polypeptide consisting of SEQ ID NOs: 3 or 4, a fragment or variant thereof or a pharmaceutically acceptable salt thereof is administered to a subject afflicted with alcohol abuse disorder to promote cessation of alcohol consumption in the subject. In another embodiment, a polypeptide comprising 85, 86, 87, 88, 89, 90, 91, 92, 93, 94, 95, 96, 97, 98 or 99% identity to SEQ ID NOs: 3 or 4, or a pharmaceutically acceptable salt thereof is administered to a subject with alcohol abuse disorder to promote cessation of alcohol consumption in the subject. In another embodiment, a polypeptide consisting of 85, 86, 87, 88, 89, 90, 91, 92, 93, 94, 95, 96, 97, 98 or 99% identity to SEQ ID NOs: 3 or 4, or a pharmaceutically acceptable salt thereof is administered to a subject with alcohol abuse disorder to promote cessation of alcohol consumption in the subject.

In another embodiment, a polypeptide consisting essentially of SEQ ID NOs: 5, 6, 7, 8, 9, or 10, or a pharmaceutically acceptable salt thereof is administered to a subject afflicted with alcohol abuse disorder to promote cessation of alcohol consumption in the subject.

The polypeptides of the invention (e.g., Spexin, a polypeptide comprising SEQ ID NOs: 1, 3, 4, 5, 6, 7, 8, 9, or 10, a fragment or variant thereof, or a pharmaceutically acceptable salt thereof) can be administered in a therapeutically effective amount. For example, an amount that is sufficient to treat alcohol abuse disorder, such as by ameliorating symptoms associated with alcohol abuse disorder (e.g., reducing alcohol consumption, promoting cessation of alcohol consumption), and/or also lessening the severity or frequency of alcohol consumption.

The amount which will be therapeutically effective in the treatment of a particular individual's disorder or condition will depend on the symptoms and severity of the disease, and can be determined by standard clinical techniques. In vitro or in vivo assays can also be used to identify optimal dosage ranges. The precise dose to be used in the formulation will also depend on the route of administration, and the severity of the alcohol abuse disorder, and should be decided according to the judgment of a practitioner and each patient's circumstances. Effective doses can be extrapolated from dose-response curves derived from in vitro or animal model test systems.

Administration and Dosing

Spexin (e.g., SEQ ID NOs: 1-10, and fragments or variants thereof) can be administered to the subject one time (e.g., as a single injection or deposition). Alternatively, Spexin (e.g., SEQ ID NOs: 1-10, and fragments or variants thereof) can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. Furthermore, Spexin (e.g., SEQ ID NOs: 1-10, and fragments or variants thereof) can be co-administrated with another therapeutic.

Spexin (e.g., SEQ ID NOs: 1-10, and fragments or variants thereof) can be administered to a subject by any means suitable for delivering Spexin (e.g., SEQ ID NOs: 1-10, and fragments or variants thereof) to cells of the subject. For example, Spexin (e.g., SEQ ID NO: 2, and fragments or variants thereof) can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with alcohol abuse disorder by any means that produce contact of the active ingredient with the agent's site of action in the body of a human or non-human subject. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. (20$^{th}$ ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Pharmaceutical formulations of the invention can comprise Spexin (e.g., SEQ ID NOs: 1-10, and fragments or variants thereof) (e.g., 0.1 to 90% by weight), or a physiologically acceptable salt thereof, mixed with a pharmaceutically-acceptable carrier. The pharmaceutical formulations of the invention can also comprise Spexin (e.g., SEQ ID NOs: 1-10, and fragments or variants thereof) which are encapsulated by liposomes and a pharmaceutically-acceptable carrier. Useful pharmaceutically-acceptable carriers are water, buffered water, normal saline, 0.4% saline, 0.3% glycine, or hyaluronic acid.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, or magnesium carbonate.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, or magnesium carbonate. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable, or synthetic origin, e.g., peanut oil, soybean oil, mineral oil, or sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Nucleic acids, peptides, small molecules, or polypeptides of the invention, when administered orally, can be protected from digestion. This can be accomplished either by complexing the nucleic acid, peptide, or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix, Pharm Res. 13: 1760-1764, 1996; Samanen, J. Pharm. Pharmacol. 48: 119-135, 1996; U.S. Pat. No. 5,391,377, describing lipid compositions for oral delivery of therapeutic agents (for example, liposomal delivery). In one embodiment, Spexin or a Spexin modulating compound can be delivered to the alimentary canal or intestine of the subject via oral administration that is can withstand digestion and degradation.

For oral administration, the therapeutic compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active agent. For buccal administration, the therapeutic compositions can take the form of tablets or lozenges formulated in a conventional manner. For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflate or can be formulated containing a powder mix of the therapeutic agents and a suitable powder base such as lactose or starch.

Spexin (e.g., SEQ ID NOs: 1-10, and fragments or variants thereof) can be delivered in a controlled release system. For example, the polypeptide can be administered using intravenous infusion, an implantable osmotic pump, a transdermal patch, liposomes, or other modes of administration. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The therapeutic compositions can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Suitable enteral administration routes for the present methods include oral, rectal, or intranasal delivery. Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. For example, Spexin (e.g., SEQ ID NOs: 1-10, and fragments or variants thereof) of the invention can be administered by injection, infusion, or oral delivery.

In addition to the formulations described previously, the therapeutic compositions can also be formulated as a depot preparation. Such long acting formulations can be administered by implantation (for example subcutaneously or intramuscularly) or by intramuscular injection. For example, the therapeutic compositions can be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents can be used to facilitate permeation. Transmucosal administration can be through nasal sprays or using suppositories. For topical administration, the compositions of the invention are formulated into ointments, salves, gels, or creams as generally known in the art. A wash solution can be used locally to treat an injury or inflammation to accelerate healing. For oral administration, the therapeutic compositions are formulated into conventional oral administration forms such as capsules, tablets, and tonics.

A composition of the present invention can also be formulated as a sustained and/or timed release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the present invention.

In the present methods, Spexin (e.g., SEQ ID NOs: 1-10, and fragments or variants thereof) can be administered to the subject either as RNA comprising sequences which expresses the gene product, in conjunction with a delivery reagent, or as a nucleic acid (e.g., a recombinant plasmid or viral vector) comprising sequences which expresses the gene product. Suitable delivery reagents for administration of Spexin (e.g., SEQ ID NOs: 1-10, and fragments or variants thereof) include the Mirus Transit TKO lipophilic reagent; lipofectin; lipofectamine; cellfectin; or polycations (e.g., polylysine), or liposomes.

The dosage administered can be a therapeutically effective amount of the composition sufficient to result in amelioration of symptoms of alcohol abuse disorder in a subject, and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In one embodiment, Spexin (e.g., SEQ ID NOs: 1-10, and fragments or variants thereof) is administered at a dose so as to achieve a plasma concentration of about 10 ng/ml to about 20 ng/ml in patients afflicted with alcohol abuse disorder. In some embodiments, the effective amount of the administered Spexin (e.g., SEQ ID NOs: 1-10, and fragments or variants thereof) is at least about 1 ng/ml, at least about 2 ng/ml, at least about 3 ng/ml, at least about 4 ng/ml, at least about 5 ng/ml, at least about 7.5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 60 ng/ml, at least about 70 ng/ml, at least about 80 ng/ml, at least about 90 ng/ml, at least about 100 ng/ml, at least about 125 ng/ml, at least about 150 ng/ml, at least about 175 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 600 ng/ml, at least about 700 ng/ml, at least about 800 ng/ml, at least about 900 ng/ml, at least about 1000 ng/ml, at least about 1250 ng/ml, at least about 1500 ng/ml, at least about 1750 ng/ml, at least about 2000 ng/ml, at least about 2500 ng/ml, at least about 2750 ng/ml, at least about 3000 ng/ml, at least about 3500 ng/ml, at least about 3750 ng/ml, at least about 5000 ng/ml, at least about 7500 ng/ml, or at least about 10,000 ng/ml. In one embodiment, Spexin (e.g., SEQ ID NOs: 1-10) is administered at a dose of 0.2 ml of Spexin a day (2500 ng/mL). In another embodiment, Spexin (e.g., SEQ ID NOs: 1-10, and fragments or variants thereof) is administered by daily intraperitoneal (IP) injection.

In one embodiment, Spexin (e.g., SEQ ID NOs: 1-10, and fragments or variants thereof) is administered at least once daily. In another embodiment Spexin (e.g., SEQ ID NOs: 1-10, and fragments or variants thereof) is administered at least twice daily. In some embodiments, Spexin (e.g., SEQ ID NOs: 1-10, and fragments or variants thereof) is administered for at least 1 week, for at least 2 weeks, for at least 3 weeks, for at least 4 weeks, for at least 5 weeks, for at least 6 weeks, for at least 8 weeks, for at least 10 weeks, or for at least 12 weeks. In further embodiments, Spexin (e.g., SEQ ID NOs: 1-10, and fragments or variants thereof) is administered in combination with a second therapeutic agent.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

A therapeutically effective dose of Spexin (e.g., SEQ ID NOs: 1-10, and fragments or variants thereof) can depend upon a number of factors known to those of ordinary skill in the art. The dose(s) of Spexin (e.g., SEQ ID NOs: 1-10, and fragments or variants thereof) can vary, for example, depending upon the identity, size, and condition of the subject or sample being treated, further depending upon the route by which the composition is to be administered, if applicable, and the effect which the practitioner desires Spexin (e.g., SEQ ID NOs: 1-10, and fragments or variants thereof) to have. These amounts can be readily determined by a skilled artisan.

Gene Therapy and Protein Replacement Methods

The invention provides methods for treating alcohol abuse disorder in a subject. In one embodiment, the method can comprise administering to the Spexin (e.g., SEQ ID NOs: 1-10, and fragments or variants thereof), which can be a polypeptide, or a nucleic acid encoding a polypeptide.

A nucleic acid encoding Spexin (such as SEQ ID NO: 2), or a functional part thereof (such as a nucleic acid encoding SEQ ID NOs: 3, 4, 5, 6, 7, 8, 9, or 10) can be introduced into the cells of a subject. For example, the wild-type Spexin gene (or a functional part thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extra-chromosomal. Integration can occur randomly or at precisely defined sites, such as through homologous recombination. For example, a functional copy of the Spexin gene can be inserted in replacement of an altered version in a cell, through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

Delivery of nucleic acids into viable cells can be effected ex vivo, in situ, or in vivo by use of vectors, and more specifically viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Biandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Non-limiting examples of in vivo gene transfer techniques include transfection with viral (e.g., retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; and U.S. Application Publication Nos. 2002/0077313 and 2002/00069, which are all hereby incorporated by reference in their entireties. For additional reviews of gene therapy technology, see Friedmann, Science, 244: 1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2): 108-15; Herweijer et al., Gene Ther. 2007 January; 14(2):99-107; Eliyahu et al., Molecules, 2005 Jan. 31; 10(1):34-64; and Altaras et al., Adv Biochem Eng Biotechnol. 2005; 99:193-260, all of which are hereby incorporated by reference in their entireties.

Protein replacement therapy can increase the amount of protein by exogenously introducing wild-type or biologically functional protein by way of infusion. A replacement polypeptide can be synthesized according to known chemical techniques or can be produced and purified via known molecular biological techniques. Protein replacement therapy has been developed for various disorders. For example, a wild-type protein can be purified from a recombinant cellular expression system (e.g., mammalian cells or insect cells, see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

These methods described herein are by no means all-inclusive, and further methods to suit the specific application is understood by the ordinary skilled artisan. Moreover, the effective amount of the compositions can be further approximated through analogy to compounds known to exert the desired effect.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided herein to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Spexin Therapy for the Treatment of Alcohol Abuse Disorder

Animals (C57BL/6J mice) were offered two options for drinking water, one bottle with pure water, and the other bottle containing a 10% ethanol/water mix, both of which were available "free choice" from Day 1 of the experiment. The males of this strain of mice are known to demonstrate a preference for alcohol when it is available to them. In this experiment, as the mice became accustomed to the 10% ethanol mix offered, they began to drink more and more of the ethanol mix, so that when their liquid consumption was plotted as a ratio of 10% ethanol/water, the ratio quickly became greater than 1 (more 10% ethanol than pure water). The mice were allowed to establish a baseline consumption pattern, and after 30 Days, 5 cages consistently consumed more of the ethanol mix than pure water.

Beginning on Day 33, three cages were treated with Spexin at 25 micrograms/kg/day in 1×PBS; via IP injection (cages 1, 4, and 10). Mice were administered the 14 amino acid Spexin peptide with carboxy terminal amidation: Asn-Trp-Thr-Pro-Gln-Ala-Met-Leu-Tyr-Leu-Lys-Gly-Ala-Gln-NH2 (SEQ ID NO: 4; available from Phoenix Pharmaceuticals, Catalog No. 023-81). The other two cages (2 and 7) were injected with an equal volume of vehicle according to the same schedule. Animals were injected for 5 days (Days 33 through 37), then given two days off (Days 38 and 39), then injected again with Spexin for two more days (days 40 and 41). While little effect was noted in the consumption patterns of the vehicle-injected animals (cages 2 and 7), a major difference was seen in the consumption pattern of the spexin-treated animals (cages 1, 4 and 10), where the ratio of ethanol/water mix dropped in all three cages, with the ratios dropping below 1 for cages 4 and 10 (FIG. 1). Note that these trends reversed on the days that the animals were not treated with Spexin (Days 38 and 39, and especially Days 43 and 44).

The results described herein show that spexin-treatment can interfere with free-choice ethanol consumption, and that the Spexin peptide (or related derivatives), can be used as a therapeutic treatment for alcohol abuse disorder.

Example 2—Spexin Reduces Ethanol Consumption in Mice

Spexin is a novel human adipokine that produces weight loss when injected into obese (DIO) mice. Its mechanisms of action include central effects, e.g. appetite suppression, mediated by the GALR2 receptor, and direct, local inhibition of long chain fatty acid (LCFA) uptake by adipocytes. By contrast, galanin is a structurally related adipokine that, by interaction with GALR2, increases appetite in mice, especially for fatty foods, and also stimulates ethanol intake. Spexin's appetite-reducing effects are mediated by competition with galanin for binding to GALR2. This suggested that galanin's stimulatory effects on ethanol intake might also be reduced by spexin.

To test this hypothesis, 5 groups of 5 male C57BL/6J mice (25 total) were housed for 40 days in plastic cages with 2 water bottles each: one containing water and the other 10% ethanol in water (10% ethanol). Fluids were available "free choice", and intake from each bottle was recorded daily.

Over the 1st week, 10% ethanol and water were consumed at a mean ratio of 0.80±0.32:1.0. Intake of 10% ethanol then increased, plateauing at a 10% ethanol:water ratio of 2.0±0.17:1.0 by Days 22-30. This was assigned a value of 100% as baseline for the subsequent studies. Starting on Day 31, 15 mice were injected with Spexin in 1×PBS 25 µg/kg in PBS i.p. daily for 3 days. Mice were administered the 14 amino acid Spexin peptide with carboxy terminal amidation: Asn-Trp-Thr-Pro-Gln-Ala-Met-Leu-Tyr-Leu-Lys-Gly-Ala-Gln-NH2 (SEQ ID NO: 4; available from Phoenix Pharmaceuticals, Catalog No. 023-81). The other 10 mice were injected with 1×PBS (vehicle) alone. Over the 3 days of injections the 10% ethanol:water ratio did not change in the PBS group, ranging from 92-95% of baseline, but fell rapidly & significantly in the spexin group from 100% to 80.7, 42.4, & 42.4% (p=0.02, 0.02, and 0.03) over the 3 days of Spexin administration (Days 33-35), rebounding to 100% and 136% in the first 2 days post-Spexin.

Offered free choice, C57BL/6J mice consume 80-200% as much 10% ethanol as water, but daily spexin injections rapidly & significantly reduce ethanol intake in these mice. The data support the idea that spexin decreases ethanol intake by competing with galanin for binding to GALR2, and has therapeutic implications for treatment of alcohol abuse disorder in man.

What is claimed is:

1. A method for treating alcohol abuse disorder in a subject, the method comprising administering to a subject an effective amount of Spexin, wherein the Spexin is a polypeptide comprising SEQ ID NO: 1, or a pharmaceutically acceptable salt thereof.

2. A method for reducing alcohol consumption in a subject afflicted with alcohol abuse disorder, the method comprising administering to the subject an effective amount of Spexin, wherein the Spexin is a polypeptide comprising SEQ ID NO: 1, or a pharmaceutically acceptable salt thereof.

3. A method for promoting the cessation of alcohol consumption in a subject afflicted with alcohol abuse disorder, the method comprising administering to the subject an effective amount of Spexin, wherein the Spexin is a polypeptide comprising SEQ ID NO: 1, or a pharmaceutically acceptable salt thereof.

* * * * *